United States Patent [19]

Hodorek et al.

[11] Patent Number: 4,795,468
[45] Date of Patent: Jan. 3, 1989

[54] MECHANISM AND METHOD FOR LOCKING A BEARING INSERT TO THE BASE OF A PROSTHETIC IMPLANT

[75] Inventors: Robert A. Hodorek; Terry D. Schlotterback, both of Warsaw, Ind.

[73] Assignee: Zimmer, Inc., Warsaw, Ind.

[21] Appl. No.: 137,128

[22] Filed: Dec. 23, 1987

[51] Int. Cl.⁴ ............................ A61F 2/30; A61F 2/38
[52] U.S. Cl. ......................................... 623/18; 623/20
[58] Field of Search ...................... 623/18, 20, 22, 19, 623/21; 24/104, 297, 621, 662, 704; 403/316, 319, 326, 348, 352, 381

[56] References Cited

U.S. PATENT DOCUMENTS

| | | | |
|---|---|---|---|
| Re. 28,895 | 7/1976 | Noiles | 3/1.912 |
| 621,029 | 3/1899 | Canda | 403/352 |
| 2,688,173 | 9/1954 | Van Peet | 24/704 |
| 3,107,409 | 10/1963 | Arthaud et al. | 24/662 |
| 3,535,204 | 10/1970 | Truxa | 403/381 X |
| 3,868,730 | 3/1975 | Kaufer et al. | 3/1 |
| 3,958,278 | 5/1976 | Lee et al. | 3/1.911 |
| 4,016,606 | 4/1977 | Murray et al. | 3/1.911 |
| 4,207,627 | 6/1980 | Cloutier | 3/1.911 |
| 4,216,549 | 8/1980 | Hillberry et al. | 3/1.911 |
| 4,240,162 | 12/1980 | Devas | 623/20 |
| 4,241,463 | 12/1980 | Khovaylo | 3/1.913 |
| 4,257,129 | 3/1981 | Volz | 3/1.911 |
| 4,353,135 | 10/1982 | Forte et al. | 3/1.911 |
| 4,380,090 | 4/1983 | Ramos | 3/1.912 |
| 4,462,120 | 7/1984 | Rambert et al. | 3/1.911 |
| 4,470,158 | 9/1984 | Pappas et al. | 3/1.911 |
| 4,501,031 | 2/1985 | McDanial et al. | 3/1.911 |
| 4,504,168 | 3/1985 | Miller | 24/704 X |
| 4,550,448 | 11/1985 | Kenna | 623/16 |
| 4,578,081 | 3/1986 | Harder et al. | 623/22 |
| 4,673,407 | 6/1987 | Martin | 623/20 |
| 4,673,408 | 6/1987 | Grobbelaar | 623/20 |
| 4,711,639 | 12/1987 | Grundei | 623/20 |
| 4,714,474 | 12/1987 | Brooks, Jr. et al. | 623/20 |
| 4,731,087 | 3/1988 | Sculco et al. | 623/21 |

FOREIGN PATENT DOCUMENTS

| | | |
|---|---|---|
| 0032828A2 | 7/1981 | European Pat. Off. |
| 0177776A2 | 4/1986 | European Pat. Off. |
| 0177755A1 | 4/1986 | European Pat. Off. |
| 2116848A | 10/1983 | United Kingdom |
| 2129306A | 5/1984 | United Kingdom |

OTHER PUBLICATIONS

Zimmer, Inc., brochure—"The Miller/Galante Porous Tivanium Total Knee–Because No Two Knees are Exactly Alike"–1984.
Depuy brochure—"Synatomic VF Tibial Plateau"–1985.
Howmedica brochure—"The P.C.A. Total Knee System Featuring T.D.T. Porous Coating"–1981.
Biomet advertisement—"The Oxford Meniscal Knee"—British JBJS, Aug. 1986.

Primary Examiner—Vincent Millin
Assistant Examiner—David J. Bender
Attorney, Agent, or Firm—Margaret L. Geringer

[57] ABSTRACT

A mechanism and method for locking or securing a bearing insert to the base of a prosthetic implant. The prosthetic implant is for replacement of a portion of natural bone at a point of articulation. The implant includes a locking mechanism which enables the bearing insert to be removably secured to the base support. The locking mechanism includes a resilient locking clip which is predisposed on one side of either the bearing insert or the base support such that when the bearing insert and base support are assembled together, the clip extends between both the insert and the support to secure the two components together. To insert and/or remove the bearing insert from the support, the clip is caused to substantially fully recede into the component in which it is predisposed. The method of securing the insert to the base includes inserting a lip extending from one side of one of the components into a corresponding cavity in the other component. The resilient clip which is located on the opposite side of one of the components is then deflected to enable the bearing insert to be installed onto the base support. The clip then relaxes back into engagement with both the insert and the base creating an interference therebetween to secure the insert to the base support.

26 Claims, 2 Drawing Sheets

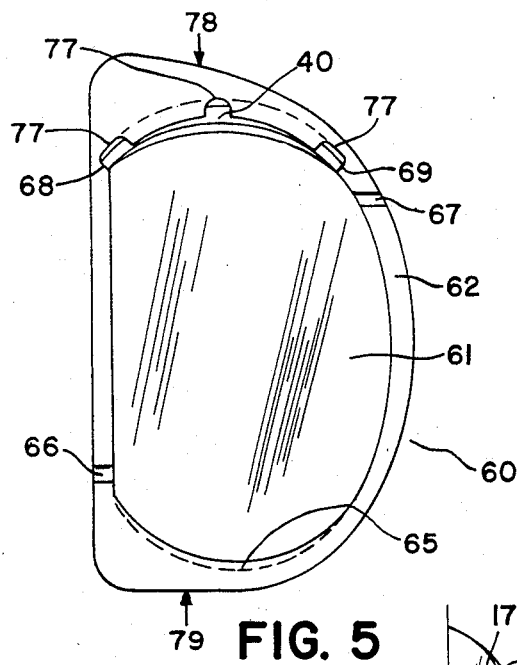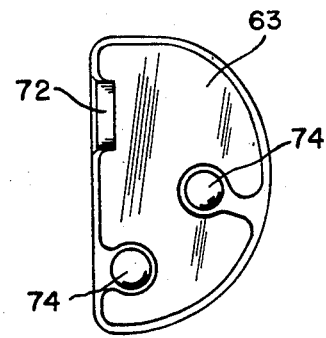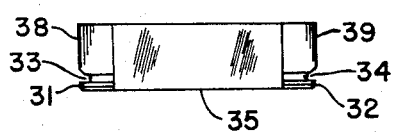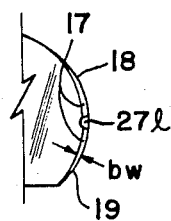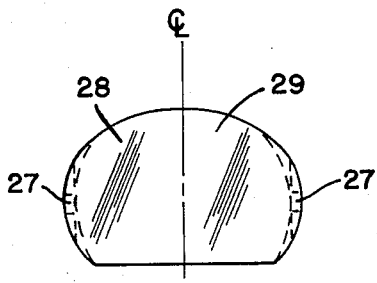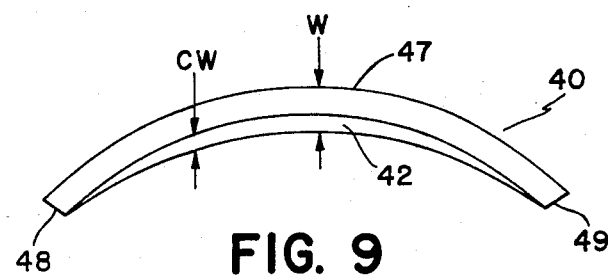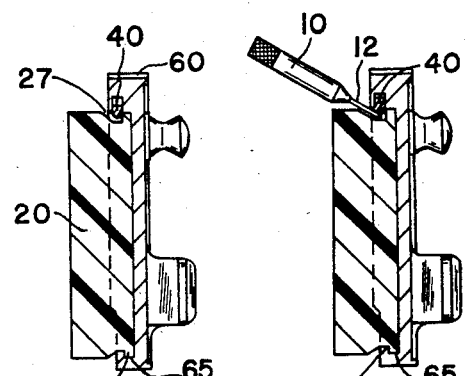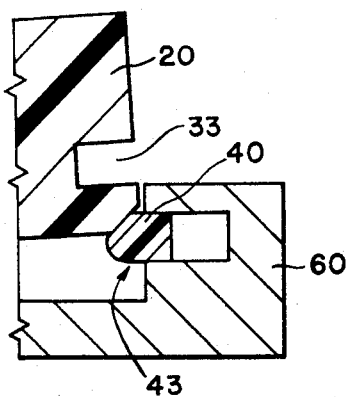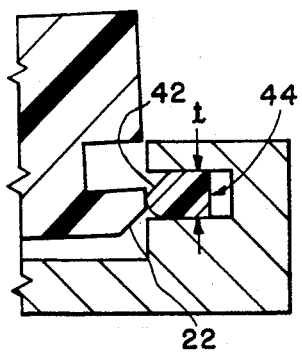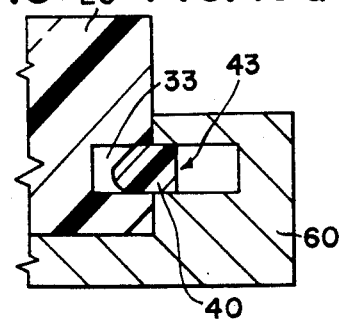

MECHANISM AND METHOD FOR LOCKING A BEARING INSERT TO THE BASE OF A PROSTHETIC IMPLANT

BACKGROUND OF THE INVENTION

The present invention relates to a prosthetic implant device, and more particularly to such implants which include a bearing insert or articulation member attached to a base support or reinforcing member. This invention is particularly suitable for use as a tibial component of a knee implant prosthesis, although is not limited thereto.

Heretofore, numerous ways have been utilized to secure an articulating bearing insert to a base support. One such example is U.S. Pat. No. 4,501,031 to McDaniel et al. which discloses a means of molding the articulating surface onto the base support to permanently secure this surface to the base support. Alternatively, it is noted that bearing inserts may be removably attached to a base support as shown in various ways by the following documents. U.S. Pat. No. 3,958,278 to Lee et al. discloses a tibial component which includes a removable E-shaped portion 25 on the base support which enables insertion or removal of the bearing insert 29. U.S. Pat. No. 4,016,606 to Murray et al. discloses a bearing insert which slides into a base support and is then secured by a locking pin inserted through both the insert and support. U.S. Pat. No. 4,207,627 to Cloutier discloses a replaceable bearing insert which has a lip which interlocks with a recess in the base support. U.S. Pat. No. 4,257,129 to Volz discloses a bearing insert which is slidably received onto a base support and then secured by a removable horizontal clip disposed about a removable vertical pin. U.S. Pat. No. 4,470,158 to Pappas et al. discloses a circular snap-ring (see FIGS. 10, 3–5 and 7–9) to unit prosthetic components. Groove 25 in component 11 retains snap-ring 24 when nonmetallic bearing insert 12 is positioned within component 11. The insert 12 can be removed by spreading the ears 23 apart through aperture 22 in component 11. It is noted that the single snap-ring 24 and corresponding grooves substantially fully encircle or surround the components which have circular attachment configurations. European Pat. No. EP 0 032 828 A2 to Lindstrand et al. discloses a bearing portion which is deformable to provide a releasable snap fit connection to the base support.

OBJECTS OF THE INVENTION

A principle object of this invention is to provide a locking mechanism to engage two mating prosthetic components and secure them together in a manner which is simple and convenient.

Another object of the invention is to preferably provide such a locking mechanism which also allows for subsequent separation of the mating components in a simple and convenient manner.

Another object of the invention is to provide a resilient locking clip disposed at one side of the implant extending between the two components to secure the two components together.

A further object of the invention is to provide such a clip which limits its engagement between the two components so that such clip and engagement of the clip does not completely surround the implant components to provide a compact and robust structure.

A still further object of the invention is to provide a locking mechanism which allows for easy insertion (such as with manual finger pressure) of a bearing insert component into a mating base support component.

Another object of the invention is to provide for easy removal of the bearing insert from the base support via a small opening or notch which allows access to the clip, so that the clip can be moved from a locking engagement position to a recessed position allowing removal of the bearing insert.

SUMMARY OF THE INVENTION

The present invention provides a prosthetic implant for replacement of a portion of natural bone at a point of articulation. The implant includes a base support component and a bearing insert which is to be secured thereto, preferably in a removable manner. The implant includes a first side in which a resilient locking clip is predisposed in a first side of one of the two components with the clip being substantially contained to this first side of the implant. The clip protrudes from the first side of the one component in a first position to extend into the first side of the other of the two components, thus causing an interference interlocking between the two components to securely lock the bearing insert to the base support. The clip has a second position in which it does not extend from the one component in which it is predisposed, but is substantially fully receded within this one component. This enables the bearing insert to be inserted and removed from the base support.

The implant further includes a second side which is oppositely located from the first side. The second side includes a lip protruding from one of the two components and a corresponding cavity aligned with the lip in the other of the two components, the lip extends into the cavity for locating engagement therebetween.

The clip preferably has a length which extends around a portion of the periphery of the bearing insert when operatively engaged therewith. This portion is less than half of the overall periphery of the bearing insert.

The bearing insert is easily secured to the base support by first inserting the protruding lip on the second side into the corresponding cavity or groove. Then the first side of the bearing insert may then be lowered toward the base support until the clip which is disposed in one of the two components contacts the other of the two components. The clip is deflected from its first position to its second position enabling the first side of the bearing insert to be inserted onto the base support, thereby fully seating the insert on the base support. The clip then is able to relax back to its first position to extend between the two components to securely lock the bearing insert to the base support.

The bearing insert may subsequently be removed if desired by applying pressure to the clip to cause it to recede into its second position, enabling the first side of the bearing insert to be removed from the base support. The protruding lip on the second side of the implant is then removed from the corresponding cavity, thus separating the insert completely from the base support.

The removable feature of the insert enables the insert to be replaced, if necessary, or enables a choice of bearing inserts to be available for use on the base support having various heights or thicknesses of inserts or providing inserts having a top articularing surface with varying contours. This modularity approach of being able to select from varying inserts to secure the desired insert to a corresponding base support chosen from a possible variety of sizes/styles of base supports designed to mate therewith helps reduce inventory stocking needs. This locking mechanism also enables the implant to be designed to accommodate varying geometries and component cross-sections as desired.

BRIEF DESCRIPTION OF THE DRAWINGS

These features and objects of the invention, as well as others, will become apparent to those skilled in the art by referring to the accompanying drawings:

FIG. 5 is an enlarged top view of the base support of the tibial component of FIG. 1;

FIG. 6 is a bottom view of the base support of the tibial component of FIG. 1;

FIG. 7 is a side view of the bearing insert of the tibial component of FIG. 1;

FIG. 7a is a partial bottom view of the bearing insert of the tibial component of FIG. 1;

FIG. 8 is a top view of the bearing insert of the tibial component of FIG. 1;

FIG. 9 is an enlarged top view of the resilient clip of the tibial component of FIG. 1;

FIG. 10 is a cross-sectional view of the tibial component taken along lines 10—10 of FIG. 4;

FIG. 10a is a cross-sectional view of the tibial component taken along lines 10—10 of FIG. 4 with a removal tool shown pressing the clip toward its recessed second position.

FIGS. 11-13 are each enlarged partial cross-sectional views of the tibial component taken along lines 11—11 of FIG. 4, with FIG. 11 showing the initial insertion of the bearing insert with the clip still in its first protruding position, FIG. 12 showing the partially inserted bearing insert pressing the clip into its second recessed position, and FIG. 13 showing the fully inserted/seated bearing insert with the clip returned to its first protruding position providing interlocking between both the bearing insert and the base support.

DETAILED DESCRIPTION OF THE INVENTION

FIGS. 1-13 illustrate a particularly advantageous embodiment of a prosthetic implant including a locking mechanism in accordance with the present invention. The invention will be described with reference to a tibial prosthesis, and is particularly suitable as such. However, it is understood that the principles of the invention are suitable for other implants which include two mating interconnecting components such as a base support and a corresponding bearing member.

Figure 1:
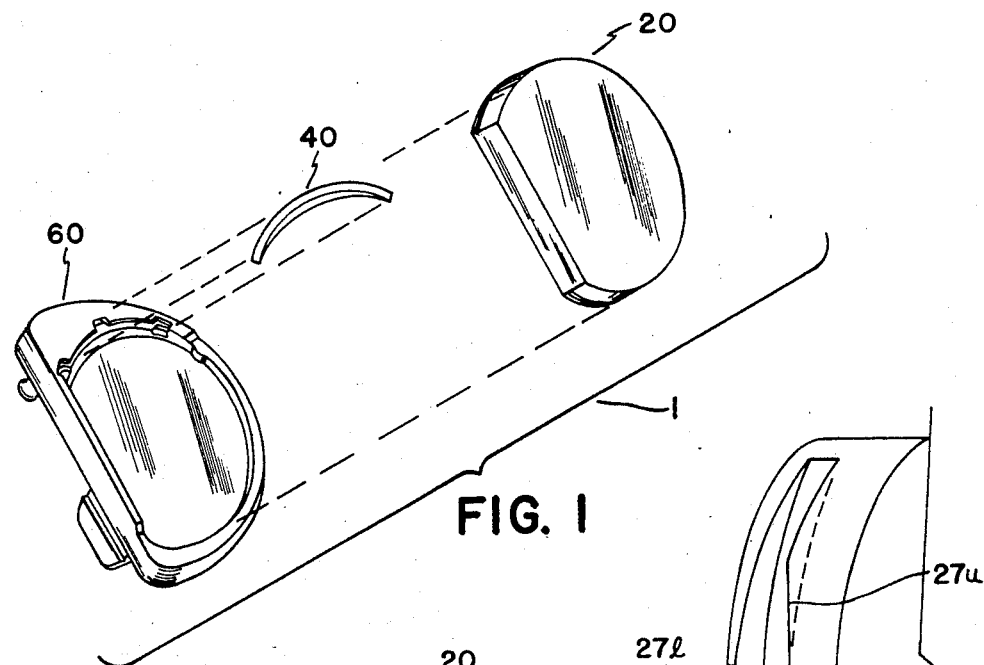
FIG. 1 is an exploded perspective view of a tibial component for a knee prosthesis in accordance with the present invention.
Figure 2:
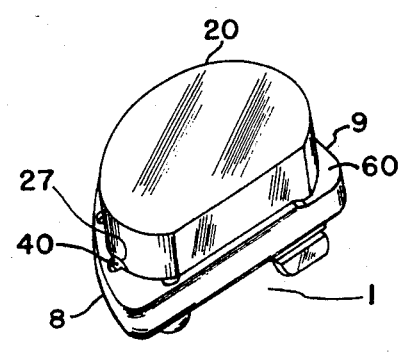
FIG. 2 is an assembled perspective view of the tibial component of FIG. 1.
Figure 7C:
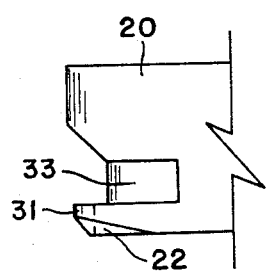
FIG. 7c is an enlarged partial side view of one end of the bearing insert FIG. 1.

The prosthetic implant 1 of FIGS. 1 and 2 includes a base support 60, a bearing insert 20 and a resilient clip 40 for securing the bearing insert 20 to the base support 60. The implant 1 includes a first side 8 and a second side 9. The first and second sides 8 and 9 are oppositely located from each other. The base support 60 includes a first side 78 corresponding to the first side 8 of the implant 1. The base support's first side includes a first cavity 64 disposed therein which is substantially contained to the first side 78. The first cavity 64 is appropriately contoured to accept a resilient clip 40 and hold the clip 40 in place in a first position 43 (see FIGS. 11 and 13) in which the clip has a portion which partially protrudes from the first cavity 64 and a second deflected position 44 (see FIG. 12) in which the clip 40 recedes substantially completely into the cavity. The bearing insert 20 includes a first groove 33 in its first side 30 which is aligned with the first cavity 64 such that when the clip 40 is in its first positio 43 and the bearing insert is operatively positioned on the base support 60, the protruding clip portion is engaged in the first groove 33 of the insert 20, thus, securely locking the insert to the base support. See FIG. 13. The groove 33 is above lip 31.

It is noted that the invention is being described with reference to a particularly advantageous embodiment in which the clip is predisposed in the base support 60 and recedes into the base support 60 to allow for insertion and removal of the bearing insert 20. However, it is understood that the principles of the invention are suitable for the clip 40 to be predisposed in the bearing insert 20 to protrude therefrom into the base support 60 and wherein the clip 40 would recede into the insert 20 to allow for insertion and removal of the insert 20. This alternate design is not shown in the Figs.; however, it is noted that the features of the invention are readily adapted to such an alternate embodiment.

The base support 60 includes a second side 79 which corresponds to the second side of the implant 9. The second side 79 is oppositely located from the first side 78. The second side 79 of the support 60 includes a separate second cavity 65 disposed therein. The second side 39 of the bearing insert 20 includes a lip 32 aligned with the second cavity 65 for locating engagement within the second cavity 65. See FIGS. 10 and 10a.

The base support 60 may include a substantially flat platform 61 with a raised rim 62 about the periphery of the platform 61 creating a receptacle area therewithin. The first cavity 64 is disposed in a first side of the rim 62 on the support's first side 78. The bearing insert 20 includes a corresponding substantially flat bottom surface 35 for seating on the platform 61 of the base support 60 within the receptacle area.

The bottom surface 35 of the bearing insert 20 has a shape which substantially corresponds to the receptacle area of the base support 60.

The second cavity 65 is disposed in a second side of the rim 62 on the support's second side 79 oppositely located from the first cavity 64 and first side of the rim 62.

The clip 40 has a chamfered upper surface 42 and the bearing insert 20 has a corresponding chamfered bottom surface 22 to enable the clip 40 to slide from its first position 43 to its second position 44 upon sliding contact between the two chamfered surfaces 42 and 22 upon application of pressure to effect such sliding, thus enabling insertion of the bearing insert. See FIGS. 11-12. Upon full insertion of the bearing, insert 20 the resilient clip 40 returns to its first position 43 to lock the bearing insert 20 to the base support 60. See FIG. 13.

Although the clp 40 could suitably be a straight, resilient member (such a straight embodiment is not shown), it is noted that the resilient clip 40 as shown in the FIGS. is preferably arcuate in shape. See FIG. 9.

The arcuate clip 40 has a first end 48 and a second end 49 interconnected by a middle portion 47. The arcuate clip 40 has an overall width "w" which is larger at the middle portion 47 and which becomes progressively thinner toward the first and second ends 48 and 49. In addition, the chamfer 42 on the clip 40 has a width "cw" which is larger at the middle portion 47 of the clip 40 and which width "cw" of the clip's chamfer 42 tapers to substantially zero toward the first and second ends 48 and 49 of the clip 40.

The chamber 22 on the bearing insert 20 has first and second ends 18 and 19 interconnected by a middle portion 17. The chamfer 22 on the insert 20 has a width "bw" which is larger at the middle portion 17 of the bearing insert's chamfer 22 and which width "bw" tapers to substantially zero toward the first and second ends 18 and 19 of the chamfer 22 of the bearing insert 20.

The clip 40 has an overall thickness "t" which is substantially constant throughout the nonchamfered portion of the clip 40.

The above described clip 40 geometry optimizes the strength of the clip 40 for the deflection it is designed to withstand. The tapering of the mating chamfers 42 on the clip and 22 on the insert is significant in that it forces the sliding action between the insert 20 and the clip 40 to occur toward the ends of the clip 40 where the spring is best supported in the first cavity 64 of the base support 60. The sliding action then migrates toward the center as the process of deflecting the clip from its first position 43 to its second position 44. The thicker middle and thinner sides of the chamfers allows the resilient clip 40 to flex, without permanent deformation.

The clip 40 and base support's clip cavity 64 and bearing insert's clip groove 33 are contained to the first side 8 of the implant, and thus do not extend around the whole periphery of the implant 1. The arcuate resilient clip 40 may be a curved circular segment, the segment being less than a semi-circular segment. Preferably, the length of the arcuate segment may be less than one-third of a circular path and potentially less than one-fourth of a circular path. The clip chamfer 42 is located on the inner radius of the circular segment.

In general, the clip 40 has a length which extends around a portion of the periphery of the bearing insert 20 when operatively engaged therewith, the portion being less than half of the overall periphery of the bearing insert 20. This allows for more flexibility in design considerations and sizes by providing a compact and robust locking mechanism. Since the clip cavity 64 and clip groove 33 do not extend substantially around the overall periphery of the implant, less material needs to be taken out for the clip cavity 64 and groove cavity 33. With the resilient clip 40 contained to one side 8 of the implant 1, this allows for great flexibility in implant design considerations. The combination of the lip 32 engaged in the second cavity 65 at the second side 9 of the implant with the resilient clip arrangement 40 at the oppositely located first side 8 provides a secure, yet simple locking mechanism. This arrangement is particularly suitable for a non-circular bearing insert 20 such as is shown in FIG. 8, although it could also be utilized with a circular insert (not shown).

In addition, the bearing insert 20, although not circular, may include a first half 28 and a second half 29 on either side 43 of center line "CL" (see FIG. 8), so that the first half 28 is a mirror image of the second half 29. The particular tibial component shown is for a unicondylar knee replacement in which the two bone condyles of the tibia of a knee are replaced by separate components instead of by one duocondylar tibial component, as is well known in the art. The mirror image of the first half 28 and second half 29 enables the bearing insert 20 shown to be usable on a base support for both the lateral and medial condyles of a tibia. For example, the base support 60 shown in FIG. 5 would be appreciated for a lateral right knee or medial left knee tibial condyle replacement. The mirror image of base support 60 (not shown) would be appropriate for a medial right knee or lateral left knee tibial condyle replacement. The bearing insert 20 shown in FIG. 8 could be utilized in either base support. It is noted that the features of this invention could also be adapted to a duocondylar tibial component (not shown), as well as to other suitable prosthetic implants which have bearing inserts to be secured to a mating base support.

Figure 7B:
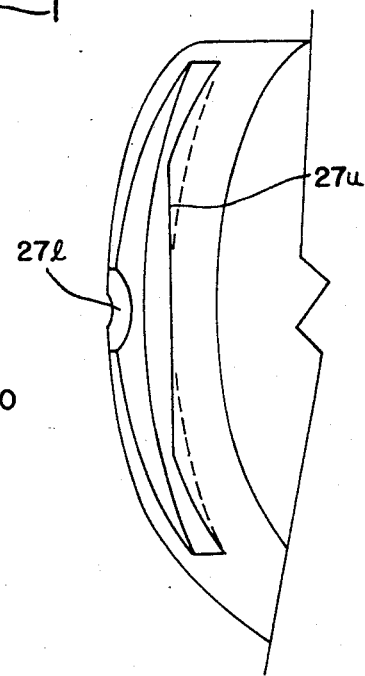
FIG. 7b is an enlarged partial perspective view of one end of the bearing insert of FIG. 1.

The bearing insert 20 includes a first notch 27 on the first side 38 of the insert 20 which accesses the first groove 33 and enables a removal tool 10 having a thin distal tip 12 to be inserted into the notch 27 and groove 33 between the clip 40 and the bearing insert 20. Application of pressure of the tool 10 on the clip 40 toward the first cavity 64 causes the clip 40 to be translated from its first position 43 to its second position 44 to enable removal of the bearing insert 20 from the base support 60. See FIG. 10a. Upon removal of the first end 38 of the insert 20 from the base support 60, the clip 40 relaxes and returns back to its original first position. As shown in FIG. 7b, the notch 27 may include a larger upper notch portion 27u and a smaller lower notch portion 27L in the lip 31.

A second notch 27 is located on the second side 39 of the bearing insert 20 which accesses a second groove 34 in keeping with the mirror-image of the first and second halves 28 and 29, so that the bearing insert 20 can be used on the mirror image base support (not shown).

It is noted that the first side 78 of the base support 60 is thicker than the second side 79 to provide more room for the first cavity 64 in which the clip 40 is retained. The rim 62 increases in height at rim ramps 66 and 64 as shown in FIG. 5.

The first cavity 64 at the first side 78 of the base support retains the resilient clip therein. The first cavity 64 includes first and second ends 68 and 69. When the clip 40 is in its first posiion 43, the clip ends 48 and 49 are supported thereagainst. The first cavity 64 is deep enough as shown in FIGS. 11–13 to allow the clip 40 to substantially completely recede into the cavity 64. When the clip is in its relaxed first position, the first cavity 64 supports the clip 40 so that approximately a width of about 1 mm extends from cavity 64 into groove 33. (The overall width "w" of such clip may be approximately 2 mm at the middle portion 47.) The first side 78 of the base support includes a plurality of notches 77 which allow some access to the first cavity 64 and which may be utilized to help release the clip 40 from cavity 64 should this be necessary.

The prosthetic implant 1 may utilize any suitable fixation means for securing the base support to the bone. FIG. 6 shows a suitable fixation means on the bottom surface 63 of the base support 60 which includes a protruding flange and two protruding pegs 74. It is understood that any suitable fixation means may be utilized.

Although any suitable implantable materials may be utilized, the base support 60 may advantageously be made from metal such as titanium, the bearing insert 20 from plastic such as ultra high molecular weight polyethylene and the clip 40 from a plastic such as PEEK (polyaryletherketone) or such as Delrin plastic. The material for the clip 40 should be able to withstand deflection without permanent deformation, thus enabling the resilient clip to perform like a spring. Certain metals may also be suitable for such a spring/clip. The spring/clip 40 is preferably retained in the base support 60 in first cavity 64 in its first position 43 in a relaxed position. It is deflected during insertion and then returns to its first relaxed position. This feature virtually eliminates problems of material creep.

Figure 3:
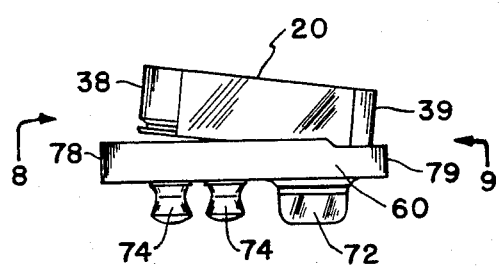
FIG. 3 is a side view of the tibial component of FIG. 1 with the bearing insert partially assembled to the base support.
Figure 4:
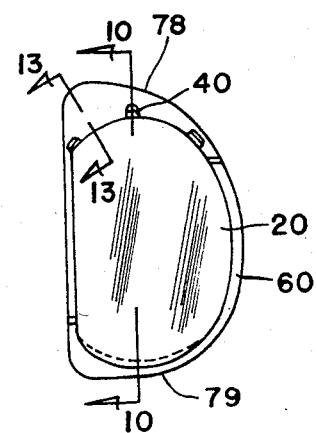
FIG. 4 is a top view of the tibial component of FIG. 1.

The following will describe the method of securing the bearing insert 20 to the base support 60. First, the lip 32 on the second side 39 of the insert 20 is inserted into corresponding second cavity 65 on the second side 9 of the implant 1. The oppositely located first side 38 of the insert 20 is lowered toward the base support 60 as shown in FIG. 3. The bottom chamfered surface 22 of the insert contacts the clip chamfer 42. See FIG. 11. Application of finger pressure is applied to cause the clip to deflect form its first position 43 to its second position 44 in which the clip 40 is substantially receded into the first clip cavity 64. See FIG. 12. The base insert 20 is then fully seated onto the base support 60 so that the first clip groove 33 is aligned with the first clip cavity 64, enabling the clip 40 to relax back to its first position 43 in which a portion of the clip 40 partially protrudes from the clip cavity 64. The clip 40 now extends between both the cavity 64 and the groove 33, thus securely locking the insert to the base support 60. See FIGS. 10 and 13.

In order to remove the insert, should this be desirable, the thin tip 12 of removal tool 10 is inserted into notch 27 between the insert 20 and clip 40. Pressure is applied to clip 40 to cause it to recede into its second position 44. See FIG. 10a. The first side 38 of the insert 20 can then be lifted off or removed from the support 60. Then the lip 32 is removed from the second cavity 65 on the base support 60, thus easily separating the insert 20 completely from support 60.

The locking mechanism for a prosthetic implant as described herein provides for a simple, but effective means for securing a bearing insert to a base support, and preferably provides a simple means for subsequent removal of the insert. While this invention has been described and exemplified in terms of a particularly advantageous embodiment, those skilled in the art can appreciate that modificatios can be made without departing from the spirit and scope of this invention.

We claim:

1. A prosthetic implant having a base support, a bearing insert, and a resilient clip for securing the bearing insert to the base support, wherein the base support includes a first side having a first cavity disposed therein, and in which the cavity accepts the resilient clip and holds the clip in place, the clip having a first position in which the clip has a portion which partially protrudes from the first cavity and a second deflected position in which the clip recedes substantially completely into the cavity, and wherein the bearing insert includes a first groove which is aligned with the first cavity such that when the clip is in its first position and the bearing insert is operatively positioned on the base support, the protruding clip portion is engaged in the first groove of the insert, thus, securely, locking the insert to the base support and wherein the base support includes a second side oppositely located from the first side, the second side including a separate second cavity disposed therein and wherein the bearing insert includes a lip aligned with the second cavity for locating engagement within the second cavity.

2. The prosthetic implant of claim 1 wherein the base support includes a substantially flat platform with a raised rim about the periphery of the platform creating a receptacle area therewithin and wherein the first cavity is disposed in a first side of the rim, and wherein the bearing insert includes a corresponding substantially flat bottom surface for seating on the platform of the base support within the receptacle area.

3. The prosthetic implant of claim 2 wherein the bottom surface of the bearing insert has a shape, substantially corresponding to the receptacle area of the base support.

4. The prosthetic implant of claim 1 wherein the prosthetic implant is a tibial component for a knee prosthesis.

5. The prosthetic implant of claim 1 wherein the bearing insert includes a first notch which accesses the first groove and enables a removal tool to be inserted into the notch and groove between the clip and the bearing insert so that the clip can be translated from its first position to its second position by the tool to enable removal of the bearing insert from the base support.

6. The prosthetic implant of claim 1 wherein the clip has a chamfered upper surface and the bearing insert has a corresponding chamfered bottom surface to enable the clip to slide from its first position to its second position upon sliding contact between the two chamfered surfaces to enable insertion of the bearing insert, and whereby upon full insertion of the bearing insert, the resilient clip returns to its first position to lock the bearing insert to the base support.

7. The prosthetic implant of claim 6 wherein the resilient clip is arcuate in shape.

8. The prosthetic implant of claim 7 wherein the arcuate resilient clip has a first end and a second end interconnected by a middle portion and wherein the clip has an overall width which is larger at the middle portion and which becomes progressively thinner toward the first and second ends.

9. The prosthetic implant of claim 7 wherein the resilient clip has a first end and a second end interconnected by a middle portion, and wherein the chamfer has a width which is larger at the middle portion and which tapers to substantially zero toward the first and second ends.

10. The prosthetic implant of claim 9 wherein the chamfer on the bearing insert has a first and second end interconnected by a middle portion, such that the middle portion of the chamfer on the bearing insert has a width that is larger at the middle portion and which tapers to substantially zero toward the first and second ends.

11. The prosthetic implnat of claim 7 wherein the clip has an overall thickness which is substantially constant throughout the nonchamfered portion of the clip.

12. The prosthetic insert of claim 1 wherein the bearing insert has a center line with a first half on one side of the center line and a second half on the other side, the first half being a mirror image of the second half.

13. The prosthetic implant of claim 12 wherein the bearing insert has a non-circular shape.

14. The prosthetic implant of claim 1 wherein clip has a length which extends around a portion of the periphery of the bearing insert when operatively engaged therewith, but the portion being less than half of the overall periphery of the bearing insert.

15. A prosthetic implant having a base support, a bearing insert, and a resilient clip for securing the bearing insert to the base support, wherein the base support includes a first side having a first cavity disposed therein, and in which the cavity accepts the resilient clip and holds the clip in place, the clip having a first position in which the clip has a portion which partially protrudes from the first cavity and a second deflected position in which the clip recedes substantially completely into the cavity, and wherein the bearing insert includes a first groove which is aligned with the first cavity such that when the clip is in its first position and the bearing insert is operatively positioned on the base support, the protruding clip portion is engaged in the first groove of the insert, thus, securely locking the insert to the base support and wherein the base support includes a substantially flat platform with a raised rim about the periphery of the platform creating a receptacle area therewithin and wherein the first cavity is disposed in a first side of the rim, and wherein the bearing insert includes a corresponding substantially flat bottom surface for seating on the platform of the base support within the receptacle area and wherein the base support includes a second side of the rim which is oppositely located from the first side of the rim and wherein the second side of the rim includes a second cavity disposed therein and wherein the bearing insert includes a lip aligned with the second cavity for locating engagement within the second cavity.

16. A prosthetic implant having a base support, a bearing insert, and a resilient clip for securing the bearing insert to the base support, wherein the base support includes a first side having a first cavity disposed therein, and in which the cavity accepts the resilient clip and holds the clip in place, the clip having a first position in which the clip has a portion which partially protrudes from the first cavity and a second deflected position in which the clip recedes substantially completely into the cavity, and wherein the bearing insert includes a first groove which is aligned with the first cavity such that when the clip is in its first position and the bearing insert is operatively positioned on the base support, the protruding clip portion is engaged in the first groove of the insert, thus, securely locking the insert to the base support and wherein the clip has a chamfered upper surface and the bearing insert has a corresponding chamfered bottom surface to enable the clip to slide from its first position to its second position upon sliding contact between the two chamfered surfaces to enable insertion of the bearing insert, and whereby upon full insertion of the bearing insert, the resilient clip returns to its first position to lock the bearing insert to the base support and wherein the resilient clip is arcuate in shape and the arcuate resilient clip is a curved circular segment, the segment being less than a semi-circular segment.

17. A prosthetic implant having a base support, a bearing insert, and a resilient clip for securing the bearing insert to the base support, wherein the base support includes a first side having a first cavity disposed therein, and in which the cavity accepts the resilient clip and holds the clip in place, the clip having a first position in which the clip has a portion which partially protrudes from the first cavity and a second deflected position in which the clip recedes substantially completely into the cavity, and wherein the bearing insert includes a first groove which is aligned with the first cavity such that when the clip is in its first position and the bearing insert is operatively positioned on the base support, the protruding clip portion is engaged in the first groove of the insert, thus, securely locking the insert to the base support and wherein the clip has a chamfered upper surface and the bearing insert has a corresponding chamfered bottom surface to enable the clip to slide from its first position to its second position upon sliding contact between the two chamfered surfaces to enable insertion of the bearing insert, and whereby upon full insertion of the bearing insert, the resilient clip returns to its first position to lock the bearing insert to the base support and wherein the resilient clip is arcuate in shape and the arcuate resilient clip is a curved circular segment in which the segment is less than one-third of a circular path in length.

18. A prosthetic implant for replacement of a portion of natural bone at a point of articulation, the implant comprising a first component of a base support and a second component of a removable bearing insert which may be positioned on the base support and a resilient locking clip, the implant includes a first side in which the clip is predisposed within a first side of one of these two components and wherein the clip protrudes from the first side of the one component in a first position to extend into the other of the two components, thus causing an interference between the two components to securely lock the bearing insert to the base support, the clip has a second position in which it does not extend from the component in which it is predisposed, thus enabling the bearing insert to be inserted onto and potentially removed from the base support and wherein the implant further includes an oppositely located second side, the second side including a lip protruding from one of the two components and a corresponding cavity aligned with the lip in the other of the two components, the lip extending into the cavity for locating engagement therebetween.

19. The prosthetic implant of claim 18 wherein the clip has a length which extends around a portion of the periphery of the bearing insert when operatively engaged therewith, but the portion being less than half of the overall periphery of the bearing insert.

20. A method of securing a prosthetic bearing insert to a base of a prosthetic implant support comprising the following steps:
   a. Inserting a protruding lip extending from one side of the bearing insert into a corresponding cavity in one side of the base support for locating engagement therebetween;
   b. Lowering an oppositely located side of the bearing insert toward an oppositely located side of the base support;
   c. Contacting the bottom chamfered surface of the oppositely located side of the bearing insert with a top chamfered surface of a resilient clip which is disposed and secured in a first position in a clip cavity on the oppositely located side of the base support in which the clip has a portion which partially protrudes from this clip cavity;
   d. Deflecting the resilient clip into a second position by pushing the two chamfered surfaces against each other, causing the clip to recede substantially completely into the clip cavity;
   e. Enabling the oppositely located side of the bearing insert to be inserted fully onto the base support; and f. Aligning a clip groove in the bearing insert with the clip cavity enabling the clip to relax back to its first position in which a portion of the clip partially protrudes from the clip cavity, the protruding portion now extending into the clip groove, thus securely locking the insert to the base support.

21. The method of claim 20 further including the following steps to enable subsequent removal of the bearing insert:
   a. Inserting a removal tool into a notch in the oppositely located side of the bearing insert between the insert and the clip;
   b. Applying pressure to the clip to cause it to recede into its second position;
   c. Removing the oppositely located side of the insert from the base support; and
   d. Removing the protruding lip of the one side of the insert from the base support, thus separating the bearing insert completely from the base support.

22. The method of securing a prosthetic bearing insert component of a prosthetic implant to a base support component comprising the following steps:
   a. Inserting a protruding lip extending from one side of one of the two components into a corresponding cavity in one side of the other component for locating engagement therebetween;
   b. Lowering an oppositely located side of the bearing insert toward an oppositely located side of the base support;
   c. Deflecting a resilient clip from a first position in which the clip is disposed and secured in a clip cavity on the oppositely located side of one of the two components and in which the clip has a portion which partially protrude from this clip cavity and into a second position in which the clip recedes substantially completely into the clip cavity;
   d. Enabling the oppositely located side of the bearing insert to be inserted fully onto the base support; and
   e. Aligning a clip groove in the oppositely located side of the other of the two components with the clip cavity enabling the clip to relax back to its first position in which a portion of the clip partially protrudes from the clip cavity, the protruding portion now extending into the clip groove, thus securely locking the insert to the base support.

23. The method of claim 22 further including the following steps to enable subsequent removal of the bearing insert:
   a. Applying pressure to the clip to cause it to recede into its second position;
   b. Removing the oppositely located side of the insert from the base support; and
   c. Removing the protruding lip from the corresponding cavity, thus separating the bearing insert completely from the base support.

24. A prosthetic implant for replacement of a portion of natural bone at a point of articulation, the implant comprising a first component of a base support and a second component of a removable bearing insert which may be positioned on the base support and a resilient locking clip, the implant includes a first side in which the clip is predisposed within a first side of one of these two components and wherein the clip is located in a first position in engagement with the base support and the bearing insert to cause an interference between the two components to securely lock the bearing insert to the base support, and wherein the clip has a second position in which the clip is deflected to enable the bearing insert to be inserted onto and potentially removed from the base support and wherein the implant further includes an oppositely located second side, the second side including a lip protruding from one of the two components and a corresponding cavity aligned with the lip in the other of the two components, the lip extending into the cavity for locating engagement therebetween.

25. The method of securing a prosthetic bearing insert component to a base support component of a prosthetic implant comprising the following steps:
   a. Inserting a protruding lip extending from one side of one of the two components into a corresponding cavity in one side of the other component for locating engagement therebetween;
   b. Lowering an oppositely located side of the bearing insert toward an oppositely located side of the base support;
   c. Deflecting a resilient clip from a first position in which the clip is disposed and secured within the oppositely located side of one of the two components into a second position in which the clip is deflected to allow the bearing insert to be inserted fully onto the base support; and
   d. Enabling the clip to relax back to its first position in which the clip is now in engagement with the base support and the bearing insert creating an interference between the two components, thus securely locking the insert to the base support.

26. The method of claim 25 further including the following steps to enable subsequent removal of the bearing insert:
   a. Applying pressure to the clip to cause it to recede into its second position;
   b. Removing the oppositely located side of the insert from the base support; and
   c. Removing the protruding lip from the corresponding cavity, thus separating the bearing insert completely from the base support.

* * * * *